United States Patent
Gaffar et al.

[11] Patent Number: 5,840,281
[45] Date of Patent: Nov. 24, 1998

[54] ORAL COMPOSITION

[75] Inventors: Abdul Gaffar, Princeton; John Afflitto, Brookside; Malathy Subramanian, Somerset, all of N.J.

[73] Assignee: Colgate Palmolive Company, New York, N.Y.

[21] Appl. No.: 288,846

[22] Filed: Aug. 11, 1994

Related U.S. Application Data

[62] Division of Ser. No. 1,480, Jan. 7, 1993, Pat. No. 5,368,845.

[51] Int. Cl.⁶ .................... A61K 7/16; A61K 7/22
[52] U.S. Cl. .................... 424/49; 424/54; 424/57
[58] Field of Search .......................... 424/49–58

[56] References Cited

U.S. PATENT DOCUMENTS

| | | | |
|---|---|---|---|
| 3,941,772 | 3/1976 | Ploger et al. | 424/54 |
| 4,693,888 | 9/1987 | Miyahara et al. | 424/49 |
| 4,816,245 | 3/1989 | Gaffar | 424/57 |
| 4,877,603 | 10/1989 | Degenhardt et al. | 424/57 |
| 5,082,653 | 1/1992 | Pan et al. | 424/54 |
| 5,135,910 | 8/1992 | Blackburn et al. | 514/2 |
| 5,217,950 | 6/1993 | Blackburn et al. | 514/2 |
| 5,260,271 | 11/1993 | Blackburn et al. | 514/2 |
| 5,296,214 | 3/1994 | Gaffar | 424/49 |
| 5,368,845 | 11/1994 | Gaffar et al. | 424/54 |

OTHER PUBLICATIONS

Howell et al J. Clin. Periodontol 20(5):335–339 May 1993 The Effect of a Mouthrinse Based on Nisin a Bacteriocin on Developing Plaque, Gingivitis.
Collison et al (I) Canada 2058455 (Jun. 22, 1992).
Collison et al (II) Canada 2055984 (Jun. 22, 1992).
Afflito et al G.B. 2274247 (Jul. 20, 1994).
Beggs et al WO/PCT9501154 (Jan. 12, 1995).
Doel et al WO/PCT 93/11738 (Jun. 24, 1993).

*Primary Examiner*—Shep K. Rose
*Attorney, Agent, or Firm*—Robert L. Stone

[57] ABSTRACT

An antiplaque composition comprising a bacteriocin such as nisin and a polyphosphonate.

20 Claims, No Drawings

ORAL COMPOSITION

This is a division of application Ser. No. 08/001,480 filed Jan. 7, 1993 now U.S. Pat. No. 5,368,845.

This invention relates to oral antiplaque compositions such as dentifrice's, mouthwashes, lozenges, chewing gums and the like. The use of nisin, or of related lanthionine-containing bacteriocins, in mouthwash and toothpaste is suggested in Blackburn et al, PCT International patent application WO 89/12399, published 28 Dec. 1989.

In accordance with one aspect of this invention, the oral composition contains the nisin together with an azacycloalkane-2, 2-diphosphonate ion, such as azacycloheptane-2, 2-diphosphonate ("AHP").

In broader aspects of the invention, other polyphosphonates may be used in place of the AHP. These include the known polyphosphonates which inhibit crystallization of hydroxyapatite and are inhibitors of the formation of dental claculus. Examples of such agents include pharmaceutically acceptable ions of azacycloalkane-2, 2-phosphonic acids, such as those in which the alkane moiety has five, six or seven carbon atoms, in which the nitrogen atom is unsubstituted (as in AHP) or carries a lower alkyl substitutent (e.g. methyl), such as those disclosed in Ploger et al U.S. Pat. No. 3,941,772. Other examples are ions of geminal diphosphonic acids such as ethanehydroxy-1, 1,-diphosphonate (EHDP), ethane-1-amino-1, 1-diphosphonate or dichloromethane-diphosphonate, as well as polymeric phosphonates such as water-soluble polymers and copolymers of vinylphosphonic acid (e.g. of molecular weight about 5000 to 30,000), including phosphonic polymers disclosed in Gaffar et al U.S. Pat. No. 5,032,386.

In place of the nisin, other lanthionine-containing peptide bacteriocins (e.g. subtilin, epidermin, cinnamycin, duramycin, anconvenin and Pep 5) may be employed, alone or in combinations of two or more such bacteriocins.

The proportion of the bacteriocin such as nisin is preferably such as to exert an antiplaque effect and the proportion of the phosphonate such as AHP is preferably such as to increase the antiplaque effectiveness of the bacteriocin. For a mouthrinse the proportion of the phosphonate may, for instance, be in the range of about 0.01% to 3%, preferably less than about 1%, e.g. within the range of about 0.05% to 0.5% such as about 0.2% or 0.3% and the proportion of the bacteriocin may, for instance, be in the range of about 0.01% to 1%, preferably about 0.03% to 0.5%. For a toothpaste (or other oral composition which, unlike a mouthrinse, becomes considerably diluted by saliva during use) the proportion of the phosphonate may, for instance, be in the range of about 0.03% to 15%, preferably within the range of about 0.15% to 6%, such as about 0.5% or 1%, and the proportion of the bacteriocin may, for instance, be in the range of about 0.01% to 5%, preferably about 0.5% to 2%.

Some aspects of the invention are illustrated in the following Examples.

EXAMPLES 1–3

A mouth rinse is prepared by mixing the following ingredients in the following proportions:

|  | 1 |  | 2 |  | 3 |
|---|---|---|---|---|---|
| Water | 70.68% |  | 77.925% |  | 82.925% |
| Sodium acetate | 0.245% |  | 0.200% |  | 0.15% |
| Aqueous 10% solution of acetic acid | 5.00% |  | 5.00% |  | 5.00% |
| 99.5% glycerol | 3.00% |  | 0 |  | 0 |
| Tween 80 | 0.40% |  | 0.40% |  | 0.40% |
| Pluronic | (F87) 0.20% | (F127) | 1.00% | (F127) | 1.00% |
| Aqueous 1% solution of nisin | 10.00% |  | 10.00% |  | 10.00% |
| 95% ethanol | 10.00% |  | 5.00% |  | 5.00% |
| Mint flavor | 0.20% |  | 0.20% |  | 0.20% |
| Sodium saccharin | 0.075% |  | 0.075% |  | 0.075% |
| Disodium salt of azacycloheptane-2, 2,-diphosphonic acid | 0.20% |  | 0.20% |  | 0.25% |

Tween 80, Pluronic F87 (Ex. 1) and Pluronic F127 (Ex. 2 and 3) are nonionic surfactants. Tween 80 is polyoxyethylene (20) sorbitan mono-oleate. The Pluronics are polyoxyethylene-polyoxypropylene-polyoxyethylene block copolymers; F87 has an average molecular weight of 7700, an HLB of more than 24 and a cloud point in aqueous 1% or 10% solution of above 100° C.; F 127 has an average molecular weight of 12600, an HLB of 18–23 and a cloud point in aqueous 1% or 10% solution of above 100° C.

The pHs of the mixtures are 4.42 (Ex. 1), 4.16 (Ex. 2) and 4.06 (Ex. 3). Example 1 gives an initially clear mixture which becomes cloudy on standing for a few hours. Examples 2 and 3 give mixtures which remain clear. Each formulation shows superior activity against plaque formation when tested in an "artificial mouth" apparatus. In that test, diluted whole human saliva is pumped continuously, at a rate of 1 ml/minute, through a chamber containing two germanium plates. This forms a pellicle on the plates. After 20 minutes the saliva flow is stopped and the mouthrinse is pumped into the chamber for 30 seconds at a flowrate of 10 ml/min., after which the saliva flow, at 1 ml/min., is resumed for 30 minutes to wash out residual mouthrinse. Then the diluted saliva, together with 10% of its volume of trypticase soy broth, is continuously pumped through the chamber at the rate of 1 ml/min. After 24 and 48 hours the same procedure (involving a 30-second mouthrinse treatment) is repeated. After 72 hours the saliva treatment is discontinued and distilled water is circulated through the chamber at a rate of 5 ml/min. for 10 minutes. The resulting washed plates are removed and allowed to air dry, and the amount of plaque formed thereon is measured by infrared spectroscopy.

In the foregoing formulations the sodium acetate and acetic acid are present to provide a pH buffer, the Tween and Pluronic components are nonionic surfactants which aid in dispersing the ingredients, the flavor is added in solution in the ethanol (which helps to solubilize it in the composition), the glycerol (a conventional humectant ingredient in mouthwashes) gives increased viscosity and a moist feel in the mouth and the saccharin is, of course, a sweetening agent.

Generally, a mouthrinse according to this invention may contain, for instance, up to about 20% of ethyl alcohol, about 0% to about 50% of humectant, about 0.1 to 5% of an emulsifying agent (surfactant), about 0% to 0.5% of a sweetening agent, about 0.03% to 0.3% of a flavoring agent.

The pH values of the oral compositions of this invention are preferably in the range of about 4 to 8, such as about 4, 4.5, 5, 5.5, 6, 6.5 or 7. The compositions are preferably acidic; e.g. the pH is below about 6 or below about 5.

The oral compositions of this invention preferably contain surfactants, such as nonionic, cationic, zwitterionic and amphoteric surfactants. Many of the suitable surfactants (surface-active agents) are disclosed in Gaffar et al U.S. Pat. No. 4,889,712; the disclosures of such agents, and their proportions (e.g. up to about 10%), in that patent are incorporated herein by reference.

Zwitterionic surfactants include quaternary ammonium, phosphonium and sulfonium compounds having an 8 to 18 carbon atom aliphatic substituent and an aliphatic substituent having an anionic water-solubilizing group (e.g. carboxy, sulfonate, sulfate, phosphate or phosphonate); one example is 4-(N,N-di(2-hydroxyethyl)-N-octadecylammonio)-butane-1-carboxylate.

Cationic surfactants include quaternary ammonium compounds having an 8 to 18 carbon atom alkyl substituent, e.g. cetyl pyridinium chloride.

Amphoteric surfactants include secondary and tertiary amines having an 8 to 18 carbon atom aliphatic substituent and an aliphatic substituent having an anionic water-solubilizing group (e.g. carboxy, sulfonate, sulfate, phosphate or phosphonate); examples are N-alkyltaurines (e.g. reaction product of dodecylamine and sodium isethionate), Miranol, etc.

The compositions of this invention may contain fluoride ion, e.g. in the form of sodium fluoride, sodium fluorophosphate, or other fluoride ion source, such as those listed in Gaffar et al U.S. Pat. No. 4,889,712; the disclosures of such fluoride ion sources, and their proportions, in that patent are incorporated herein by reference.

The amount of fluoride-providing compound is dependent to some extent upon the type of compound, its solubility, and the type of oral preparation, but it must be a nontoxic amount, generally about 0.005 to about 3.0% in the preparation. In a dentifrice preparation, e.g. dental gel, toothpaste (including cream), toothpowder, or dental tablet, an amount of such compound which releases up to about 5,000 ppm of F ion by weight of the preparation is considered satisfactory. Any suitable minimum amount of such compound may be used, but it is preferable to employ sufficient compound to release about 300 to 2,000 ppm, more preferably about 800 to about 1,500 ppm of fluoride ion. Typically, in the cases of alkali metal fluorides and stannous fluoride, this compound is present in an amount up to about 2% by weight, based on the weight of the preparation, and preferably in the range of about 0.05% to 1%. In the case of sodium monofluorophosphate, the compound may be present in an amount of about 0.1–3%, more typically about 0.76%.

In oral preparations such as mouthwash, lozenges and chewing gum, the fluoride-providing compound is typically present in an amount sufficient to release up to about 500 ppm. preferably about 25 to about 300 ppm by weight of fluoride ion. Generally about 0.005 to about 1.0 wt. % of such compound is present.

EXAMPLE 4

A toothpaste is prepared according to the following formula:

| Glycerol | 20.0% |
|---|---|
| Precipitated silica | 20.0% |
| Sodium saccharin | 0.75% |
| Sorbitol (70%) | 20.0% |
| Sodium fluoride | 0.243% |
| Tween 80 | 1.0% |
| Pluronic F127 | 1.0% |
| Mint flavor | 1.0% |
| Nisin | 1.0% |
| AHP | 1.0% |
| Hydroxyethylcellulose | Thickening amount |
| Water | Balance |

In this toothpaste formulation, the glycerol and 70% sorbitol are conventional humectants, the hydroxyethylcellulose is a conventional binder or gelling agent, and the precipitated silica is a conventional amorphous silica dental abrasive. Other humectants, binders (thickeners or gelling agents), abrasives (polishing agents), surfactants and flavoring agents may be used, such as those listed in Gaffar et al U.S. Pat. No. 4,889,712, in the proportions described in that patent, whose disclosures thereof are incorporated herein by reference.

EXAMPLE 5

A clear mouthrinse having a pH of 4.25 is prepared from the following ingredients: water 84.625%; sodium acetate 0.6%; aqueous 10% solution of acetic acid 2.6%; Tego Betain L5351 1%; Pluronic F127 1%; sodium sacharin 0.075%; nisin 0.1%; aqueous 5% solution of polyvinyl phosphonic acid (of molecular weight about 300) 10%. The Tego Betain L5351 is an aqueous solution, containing about 33% of cocamidopropyl betain, a zwitterionic surfactant commercially available from Goldschmidt Chemical Corp.

The compositions of this invention are preferably substantially free of strong chelating agents such as EDTA or citrate ions.

As indicated in the Examples the compositions of this invention contain water, e.g. 2% to 95% water. For mouthrinses the proportion of water may be, for instance, in the range of about 10 to 95% preferably about 40% to 85%. For toothpastes the water content may be, for instance, in the range of about 5 to 50% preferably about 10 to 30%.

This invention has been disclosed with respect to preferred embodiments and it will be understood that modifications and variations thereof are to be included within the spirit and purview of this application.

We claim:

1. An oral composition comprising an antiplaque amount of a lanthionine-containing bacteriocin and an antiplaque-increasing amount of a polyphosphonate which is an inhibitor of the crystallization of hydroxyapatite comprising ions of a geminal $C_{1-2}$ alkyl diphosphonate or a polymer or copolymer of vinyl phosphonic acid.

2. An oral composition as in claim 1 comprising nisin.

3. An oral composition as in claim 1 comprising an polyvinylphosphonic acid ion.

4. An oral composition as in claim 2 comprising polyvinylphosphonic acid ion.

5. An oral composition as in claim 1 having an acidic pH.

6. A composition as in claim 5 in which the pH is about 4 to 6.

7. A composition as in claim 1 containing 300–5,000 ppm F ions.

8. A composition as in claim 1 which is an aqueous mouthrinse containing about 0.05% to 0.5% of said polyphosphonate and about 0.03% to 0.5% of nisin and having a pH of about 4 to 6.

9. A composition as in claim 8 in which the polyphosphonate is polyvinylphosphonic acid ion and the proportion of said diphosphonate is about 0.2% to 0.3%.

10. Process for reducing the incidence of plaque on teeth in the mouth comprising contacting said teeth with a composition as in claim 1.

11. Process as in claim 10 in which said composition is an aqueous mouthrinse containing about 0.0% to 1% of said bacteriocin.

12. Process as in claim 10 in which said composition is an aqueous mouthrinse containing about 0.05% to 0.5% of said polyphosphonate and about 0.03% to 0.5% of nisin.

13. Process as in claim 12 in which said polyphosphonate is polyvinylphosphonic acid ion the pH is about 4 to 6, and the proportion of said polyphosphonate is about 0.2% to 0.3%.

14. An oral composition according to claim 1 in the form of a toothpaste containing about 0.03% to 15% of said polyphosphonate and about 0.01% to 5% of said bacteriocin.

15. A toothpaste composition according to claim 14 comprising polyvinylphosphonic acid and nisin.

16. A toothpaste composition according to claim 15 substantially free of strong chelating agents such as EDTA and citrate ions.

17. A mouthrinse composition according to claim 9 substantially free of strong chelating agents such as EDTA and citrate ions.

18. Process for reducing the incidence of plaque on teeth in the oral cavity comprising contacting the teeth with a composition according to claim 14.

19. Process for reducing the incidence of plaque on teeth in the oral cavity comprising contacting the teeth with a composition according to claim 15.

20. Process for reducing the incidence of plaque on teeth in the oral cavity comprising contacting the teeth with a composition according to claim 16.

* * * * *